United States Patent
Speier et al.

(10) Patent No.: US 9,485,475 B2
(45) Date of Patent: Nov. 1, 2016

(54) SURGICAL IMAGING SYSTEM AND METHOD FOR PROCESSING SURGICAL IMAGES

(71) Applicant: Arthrex, Inc., Naples, FL (US)

(72) Inventors: Craig Speier, Santa Barbara, CA (US); Bruce Laurence Kennedy, Santa Barbara, CA (US); Wei Yao, Santa Barbara, CA (US)

(73) Assignee: ARTHREX, INC., Naples, FL (US)

( * ) Notice: Subject to any disclaimer, the term of this patent is extended or adjusted under 35 U.S.C. 154(b) by 329 days.

(21) Appl. No.: 14/211,936

(22) Filed: Mar. 14, 2014

(65) Prior Publication Data

US 2014/0267658 A1 Sep. 18, 2014

Related U.S. Application Data

(60) Provisional application No. 61/799,547, filed on Mar. 15, 2013.

(51) Int. Cl.
*H04N 7/18* (2006.01)
*G06F 19/00* (2011.01)

(52) U.S. Cl.
CPC ............. *H04N 7/181* (2013.01); *A61B 90/361* (2016.02); *G06F 19/3406* (2013.01); *G06F 19/3425* (2013.01)

(58) Field of Classification Search
USPC .................................................... 348/72, 65
See application file for complete search history.

(56) References Cited

U.S. PATENT DOCUMENTS

| | | | |
|---|---|---|---|
| 5,179,651 A | 1/1993 | Taaffe et al. | |
| 6,770,027 B2 * | 8/2004 | Banik ................ | A61B 1/00016 348/65 |
| 6,791,601 B1 * | 9/2004 | Chang ...................... | H04N 7/18 348/620 |
| 7,587,467 B2 * | 9/2009 | Hesselink ............... | H04L 67/06 709/214 |
| 7,937,163 B2 * | 5/2011 | Sekiguchi .......... | A61B 1/00039 600/300 |
| 7,976,461 B2 * | 7/2011 | Ertas ................... | A61B 1/00059 600/101 |
| 8,189,993 B2 * | 5/2012 | Tashiro .................... | H04N 5/76 386/248 |
| 8,199,187 B2 * | 6/2012 | Knapp, II .......... | A61B 1/00103 348/231.3 |
| 8,199,188 B2 * | 6/2012 | Amling .................. | H04N 5/232 348/231.3 |
| 9,007,450 B2 * | 4/2015 | Amling .................. | H04N 5/232 348/231.3 |
| 2003/0093503 A1 * | 5/2003 | Yamaki ............... | G06F 19/3406 709/220 |
| 2005/0200698 A1 * | 9/2005 | Amling .............. | A61B 1/00059 348/65 |
| 2007/0027459 A1 * | 2/2007 | Horvath .............. | G06F 19/3412 606/147 |
| 2009/0046146 A1 * | 2/2009 | Hoyt ................... | A61B 1/00039 348/143 |
| 2010/0036676 A1 | 2/2010 | Safdi et al. | |
| 2013/0202209 A1 * | 8/2013 | Ariyama ................ | G06K 9/036 382/190 |

OTHER PUBLICATIONS

International Search Report and Written Opinion, dated Oct. 28, 2014.

* cited by examiner

*Primary Examiner* — Paulos M Natnael
(74) *Attorney, Agent, or Firm* — Karish & Bjorgum, PC

(57) ABSTRACT

An imaging system having at least two surgical systems, each surgical system having a camera control unit with a network port; a camera head coupled to the camera control unit; and a monitor coupled to the camera control unit; a network is coupled to the network port of each camera control unit; and a server is coupled to the network, the server having a storage device with a user database and a case database; and wherein the server is configured as a web server to provide data, video and images from the camera control units to users connected to the network.

29 Claims, 11 Drawing Sheets

FIG. 8

CASE LIST REPORT    VIDEO DASHBOARD    CASE LIST    SURGEON LIST    REPORTS    SETTINGS

PRINT  EXPORT

TIME PERIOD: CUSTOM ▽   START DATE: 01/05/2013 ▽   END DATE: 01/27/2013 ▽   🔎

| DATE | SURGEON | PROCEDURE | PATIENT | START TIME | END TIME | DURATION |
|---|---|---|---|---|---|---|
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |
| 01/27/13 | SURGEON NAME | PROCEDURE TYPE | PATIENT NAME | 10:22:10 | 12:22:20 | 2 HOURS |

FIG. 9

CASE DETAILS

| DATE | SURGEON | PROCEDURE | PATIENT | | CLOSE |
|---|---|---|---|---|---|
| 01/05/2013 | SURGEON NAME | PROCEDURE TYPE | PATIENT NAME | | |
| # OF SKILLS | VIDEO CLIPS | VIDEO DURATION | REMOTE VIEWERS | | START TIME |
| 25 | 4 | 1.5 HOURS | 0 | | 10:22:10 |
| | | | | | END TIME |
| | | | | | 1:29:04 |

EQUIPMENT USED

| TYPE | NAME | SERIAL # |
|---|---|---|
| EQUIPMENT TYPE | EQUIPMENT NAME | 23-56347890 |
| EQUIPMENT TYPE | EQUIPMENT NAME | 23-56347890 |
| EQUIPMENT TYPE | EQUIPMENT NAME | 23-56347890 |
| EQUIPMENT TYPE | EQUIPMENT NAME | 23-56347890 |
| EQUIPMENT TYPE | EQUIPMENT NAME | 23-56347890 |
| EQUIPMENT TYPE | EQUIPMENT NAME | 23-56347890 |
| EQUIPMENT TYPE | EQUIPMENT NAME | 23-56347890 |
| EQUIPMENT TYPE | EQUIPMENT NAME | 23-56347890 |

ALERT LOG

| TIME | TYPE |
|---|---|
| 10:34:03 | ALERT TYPE |
| 10:34:03 | ALERT TYPE |
| 10:34:03 | ALERT TYPE |
| 10:34:03 | ALERT TYPE |
| 10:34:03 | ALERT TYPE |
| 10:34:03 | ALERT TYPE |
| 10:34:03 | ALERT TYPE |

Fig. 10

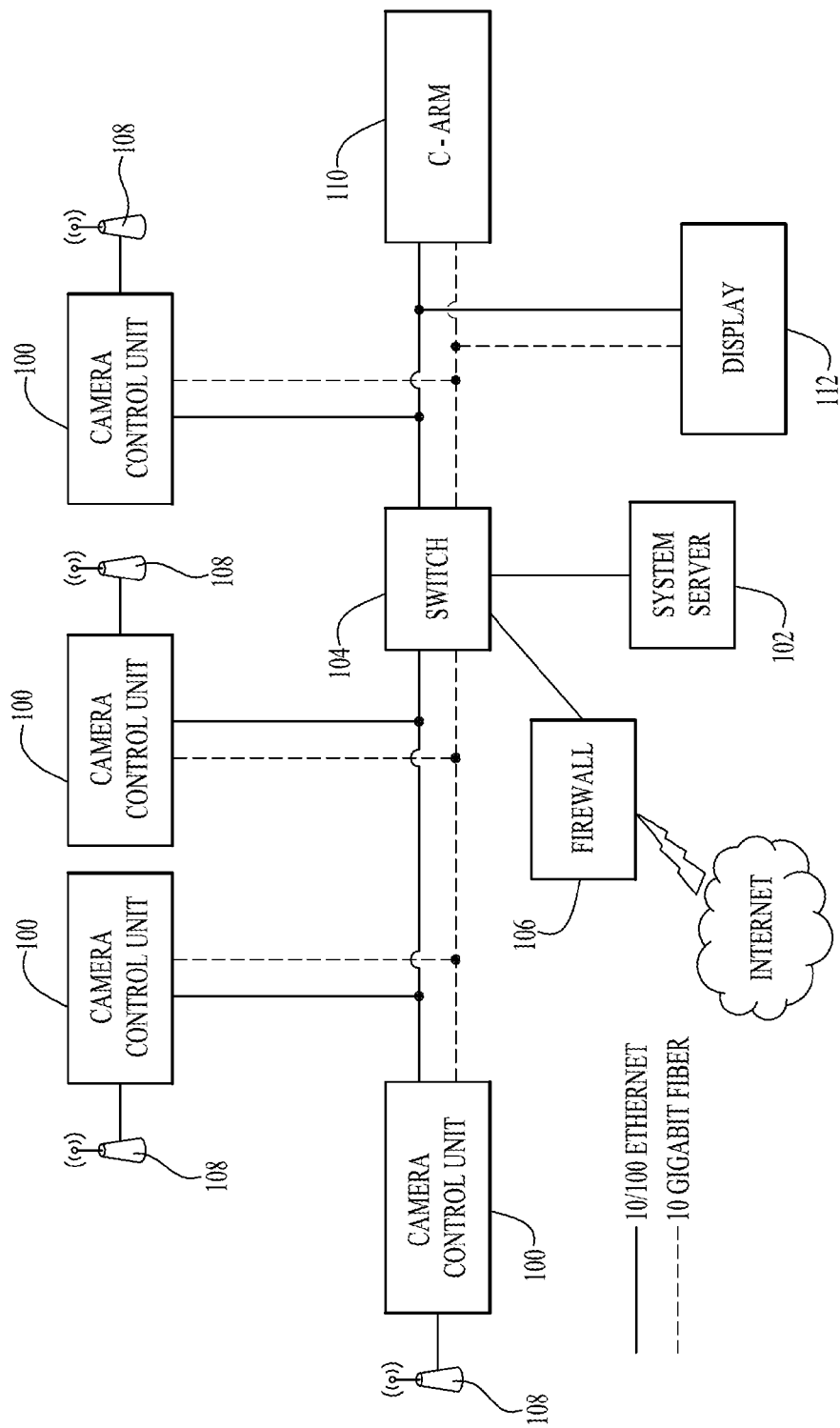

SURGICAL IMAGING SYSTEM AND METHOD FOR PROCESSING SURGICAL IMAGES

CROSS REFERENCE TO RELATED APPLICATION

This application claims priority of U.S. Provisional Patent Application No. 61/799,547, filed on Mar. 15, 2013, entitled SURGICAL IMAGING SYSTEM AND METHOD FOR PROCESSING SURGICAL IMAGES, the entire contents of which are hereby incorporated herein by reference.

BACKGROUND

The present invention relates to devices used in endoscopic surgery and, more particularly, to a network of endoscopic devices and the user experience related thereto.

Prior to a surgery, there is a desire for centralized scheduling of surgical cases, automatic delivery of patient and surgical case information from a centralized location to operating rooms, and centralized adjustment and delivery of surgeon and site surgical preferences. Pre-operative scheduling may improve operating room occupancy rates and shorten operating room preparation time.

During the course of endoscopic surgery, there is a desire for surgeons or hospital staff outside the operating room to observe the surgery and communicate with the surgeon/staff within the operating room. There exists a need for the hospital staff outside the operating room to view multiple video streams in combination with relevant data (for example, surgery time, operating room status, alerts) simultaneously to enable direct and rapid support of the surgeon and operating room staff. There exists a need to enable communication for remote viewers (such as senior surgeons and hospital staff (such as operating room managers) to view a live video stream or streams remotely and communicate with the surgeon inter-operatively in a manner that minimizes distraction to the surgeon.

Post-operatively, there is a desire for the surgeon to communicate to the patient or others the results of the surgery using images captured during surgery or video recordings made during surgery. As well, post-operatively, there is a desire for hospital management to gather data regarding the efficiency of the operating room (e.g. Surgery Time, Turn-Around Time), as well as any equipment setting changes during surgery which are necessary for medical records.

Management of post-operative artifacts (e.g. videos and still images) and data varies widely by institution. Many institutions simply print hard copies of the images for the medical records and an additional copy for the patient. Many institutions avoid recording videos due to the difficulty of managing the videos. Often, still images, videos and data are not easily available to the surgeon for post-operative management.

There exists a need for a better and more accessible way to archive surgical images, videos, and related data.

Hospitals and other institutions that perform surgery are continuously trying to improve efficiency to reduce cost. To support that effort, independent auditors or additional staff record data and report metrics such as surgery time for various procedures, surgery time for various surgeons for a particular procedure, and operating room turn-over time.

There exists a need for a way to automatically record data, produce reports for medical records and produce reports that can help managers devise strategy to improve operating room efficiency.

SUMMARY

The invention according to an embodiment, has a network of at least 2 camera control units (CCU's) connected to a system server to enable a simple user interface for: remote viewing of video/data from an operating room (or cluster of operating rooms), communication with the surgeon interoperatively, enabling cloud based archiving, and to provide analytics for reporting. The system server may be connected to the camera control units via a commercial off the shelf (COTS) infrastructure (for example, a 10/100 Ethernet connection). The system server contains a web server to enable client based interaction through any device with a web browser. This enables "out-of-the box" communication with mobile devices and reduces the burden on the customer from procuring custom devices for interacting with the system server.

An imaging system according to an embodiment of the present invention has at least two surgical systems. Each surgical system has a camera control unit, each camera control unit having a network port, a camera head coupled to the camera control unit; and a monitor coupled to the camera control unit. A network is coupled to the network port of each camera control unit. A server is coupled to the network, the server having a storage device with a user database and a case database. The server is configured as a web server to provide data and images from the camera control units to users connected to the network.

The user database may have user preferences for a camera control unit; and each camera control unit may be configurable by the system server to have the user preferences. Each surgical system may have at least one surgical device in communication with the camera control unit; the user database may have user preferences for displaying information from the at least one surgical device on the monitor; and the server may use the user preferences to configure each camera control unit to display information from the at least one surgical device on the monitor. The at least one surgical device may be selected from the group consisting of: a shaver, a pump, an ablation device, a tourniquet and an insufflator.

Optionally, each surgical system has at least one surgical device in communication with the camera control unit; the user database comprises user preferences for the at least one surgical device; and the server uses the preferences for the at least one surgical device to configure the at least one surgical device. Additionally, the server may store information from the at least one surgical device and surgical data, video and surgical images in the case database.

In an embodiment, the user database further comprises user preferences for who can view at least one of live surgical data, video and surgical images; and wherein the system server provides at least one of live surgical data, video and surgical images to users connected to the network in accordance with the user preferences. Optionally, the server is further configured to allow text messaging, audio conferencing or videoconferencing between a user connected to the network and at least one camera control unit; the user database further comprises user preferences for who can engage in text messaging, audio conferencing or videoconferencing; and wherein the server provides text messaging, audio conferencing or videoconferencing between a user connected to the network and the at least one camera control unit in accordance with the user preferences.

Optionally, the imaging system has at least one storage device coupled to the network; the user database further comprises user preferences about data, video and images stored on the storage device; and wherein the server stores data, video and images on the storage device in accordance with the user preferences about data, video and images stored on the storage device. The user database may also store user preferences for generating reports; and the server may be configured to generate reports from data, video and images in the case database for at least one of the group consisting of institutions, referring physicians, patients, surgeons and insurance companies in accordance with the user preferences for generating reports.

In an embodiment, the user database comprises user preferences for generating reports; the storage device is configured as a web server to provide data and images to users and to generate reports for at least one of the group consisting of institutions, referring physicians, patients, surgeons and insurance companies in accordance with the user preferences for generating reports. The storage device may be further configured to allow users to edit or annotate at least one of surgical data, video and images and save the edited or annotated surgical data, video and images.

Optionally, the server is configured to provide data, video and images from more than one camera control unit simultaneously to users connected to the network. Each camera control unit may be configured as a web server to provide reduced resolution video, reduced frame-rate video or still images from the camera head; and wherein the server may be configured to obtain the reduced resolution video, reduced frame-rate video or still images from the camera control unit.

An imaging system according to an additional embodiment of the present invention has at least two surgical systems. Each surgical system has a camera control unit, each camera control unit comprising a network port; a camera head coupled to the camera control unit; a monitor coupled to the camera control unit; and at least one surgical device in communication with the camera control unit. A network is coupled to the network port of each camera control unit. A server is coupled to the network, the server comprising a storage device having a user database and a case database. The server is configured as a web server to provide data and images from the camera control units to users connected to the network.

Optionally, the user database has user preferences for the at least one surgical device; the server uses the preferences for the at least one surgical device to configure the at least one surgical device; and the server uses the preferences for the at least one surgical device to configure each camera control unit to display information from the at least one surgical device on the monitor. Additionally, the server may store information from the at least one surgical device and surgical data, video and images in the case database. The at least one surgical device may be selected from the group consisting of: a shaver, a pump, an ablation device, a tourniquet and an insufflator.

The server may be configured to allow text messaging, audio conferencing or videoconferencing between a user connected to the network and at least one camera control unit; the user database further comprises user preferences for who can engage in text message, audio conferencing or videoconferencing; and wherein the system server provides text messaging, audio conferencing or videoconferencing between a user connected to the network and the at least one camera control unit in accordance with the user preferences.

An imaging system according to an additional embodiment of the present invention, has at least two surgical systems. Each surgical system has a camera control unit, each camera control unit comprising two network ports; a camera head coupled to the camera control unit; a monitor coupled to the camera control unit; and at least one surgical device in communication with the camera control unit. A first network is coupled to a first network port of each camera control unit and a second network is coupled to a second network port of each camera control unit, the second network comprising a different bandwidth than the first network. A switch is coupled to the first network and the second network. A server is coupled to the switch, the server comprising a storage device having a user database and a case database.

The server is configured as a web server to provide data and images from more than one camera control unit simultaneously to users connected to the network. The server is further configured to allow text messaging, audio conferencing or videoconferencing between a user connected to the network and at least one camera control unit. The user database further comprises user preferences for who can engage in text message, audio conferencing or videoconferencing. The server provides text messaging, audio conferencing or videoconferencing between a user connected to the network and the at least one camera control unit in accordance with the user preferences.

BRIEF DESCRIPTION OF THE DRAWINGS

The features, aspects and advantages of the present invention will become better understood with regard to the following description, appended claims and accompanying figures wherein:

FIG. 8 is a screenshot of a case report creation screen available to a local or remote user according to an embodiment of the present invention;

FIG. 9 is a screenshot of a case list report for viewing by a local or remote user according to an embodiment of the present invention;

FIG. 10 is a screenshot of a case detail screen for viewing by a local or remote user according to an embodiment of the present invention; and FIG. 11 is a schematic diagram illustrating a surgical imaging system according to an additional embodiment of the present invention employing a single switch that supports both 10/100 Ethernet and 10 gigabit (10 Gb) networks.

DETAILED DESCRIPTION

Figure 1:
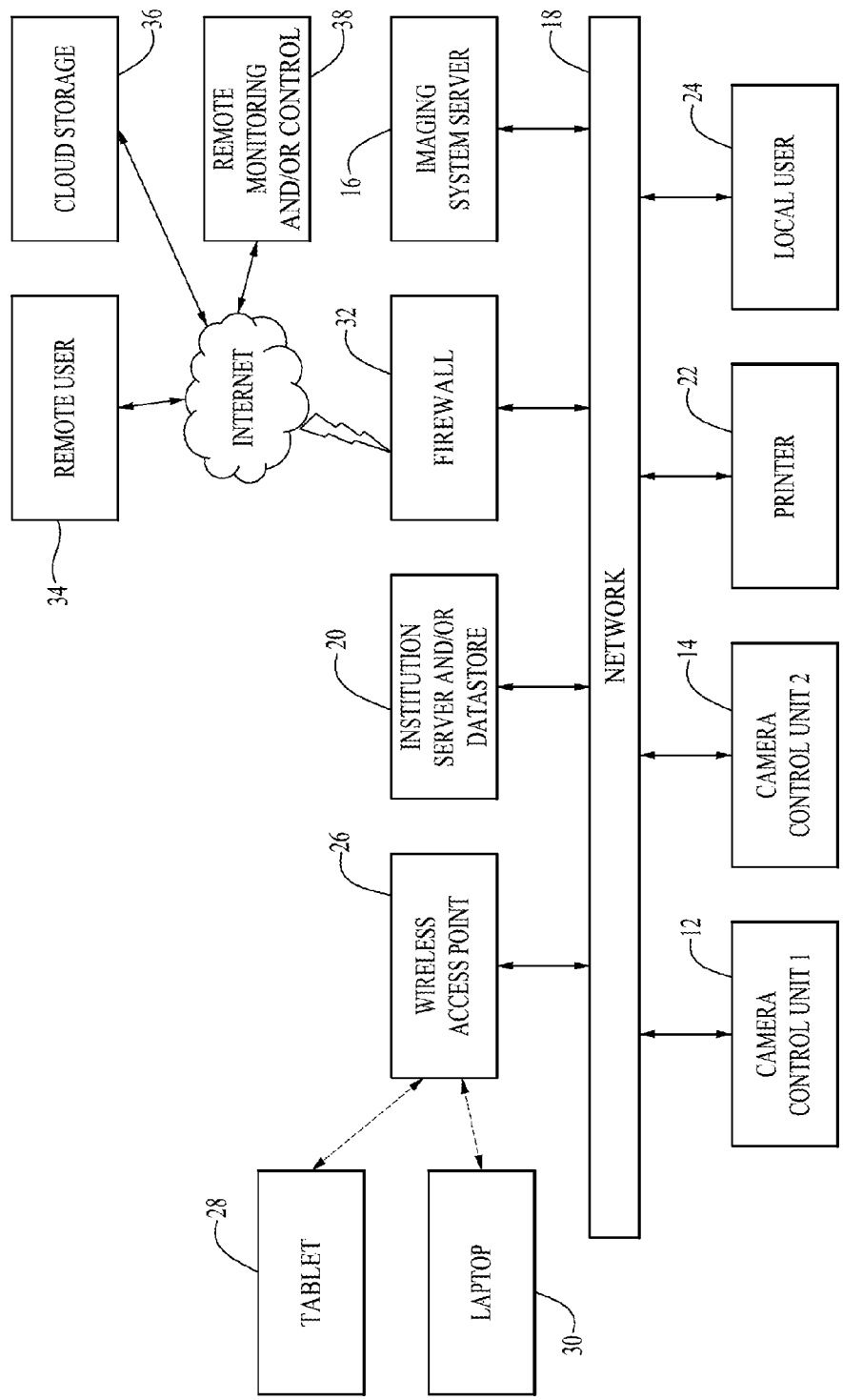
FIG. 1 is a schematic diagram illustrating a surgical imaging system according to an embodiment of the present invention.

A surgical imaging system 10 according to an embodiment of the present invention is shown in FIG. 1. The endoscopic imaging system 10 has multiple camera control units 12, 14 coupled to an imaging system server 16 via a local network 18 (e.g. cables, switches and routers). While the system has been illustrated with two camera control units, the system may accommodate many more camera control units depending on the needs of an institution using the system and the bandwidth of the institution's local network 18. The network 18 may utilize Ethernet standards (including 10 gigabit Ethernet) for communication.

At least one institution server or datastore 20 may be coupled to the network infrastructure 18. For example, the institution may have an electronic medical record (EMR) server that is connected to the network 18 and which may communicate with the system server 16. Additionally, the institution may have a picture archiving and communication system (PACS) that is connected to the network 18 and which may communicate with the system server 16. At least one shared printer 22 may be coupled to the network 18. At least one computer 24 for operation by a local user may be coupled to the network 18 via a physical connection for access to information from, for example, the camera control units and the imaging system server 16.

Additionally, at least one wireless access point 26 may be connected to the network 18. One or more computing devices, such as mobile phones, tablet computers 28, and laptop computers 30 may wirelessly connect to the network 18 via the wireless access point 26.

Additionally, a firewall 32 or similar network security technology may be connected to the network 18 to control access to the Internet and remotely located resources accessible via the Internet. For example, an authorized remote viewer 34 may access the network 18 via the Internet using a secure connection facilitated by the firewall 32. Additionally, a remotely accessible storage device or cloud storage system 36 may be accessed. Additionally, a remote monitor or control system 38 may access the network 18 through the firewall to communicate with devices on the network, for example the camera control units 12, 14 and the system server 16. The remote monitor or control system 38 may be used perform maintenance or system upgrades for devices on the network, such as the camera control units 12, 14 and the system server 16.

System configuration within an operating room according to an embodiment of the present invention will now be described in more detail with reference to FIG. 2. The camera control unit 12 is used in conjunction with a camera head 40 to view internal features of a body of a patient without the use of traditional, fully invasive surgery. In an embodiment, the camera head 40 is coupled to the camera control unit 12 via a cable 42 to facilitate data transfer between the camera head 40 and the camera control unit 12. In an alternative embodiment, the camera head 40 is wirelessly coupled to the camera control unit 12 such as via IEEE 802.11b, or IEEE 802.11n or ultra-wide band (UWB).

The camera head 40 acquires image data and transmits it to the camera control unit 12 to process a usable image. The camera head 40 may be used together with an endoscope or other medical instruments for transmitting image data. The camera head 40 has one or more imaging devices. For example, the imaging devices may include one or more charge coupled device (CCD) sensors or complementary metal-oxide-semiconductor (CMOS) sensors. The camera head 40 may further include an illumination system. The camera head 40 may also have memory for storing camera data, camera control unit processing data or other information. In an embodiment, the camera head 40 has at least one user input means, such as a button, to control aspects of image capture.

The camera control unit 12 is coupled to a monitor 44 where image data is displayed for a surgeon. The camera control unit 12 may overlay the image data with additional information for the surgeon as will be discussed further below. The camera control unit 12 is also connectable to at least one input device such as a mouse, keyboard, touchpad, or touchscreen monitor. Additionally, the camera control unit 12 may be connectable to a tablet computer, such as an Apple® iPad® or other computing device to act as an input device or an output device.

Figure 2:
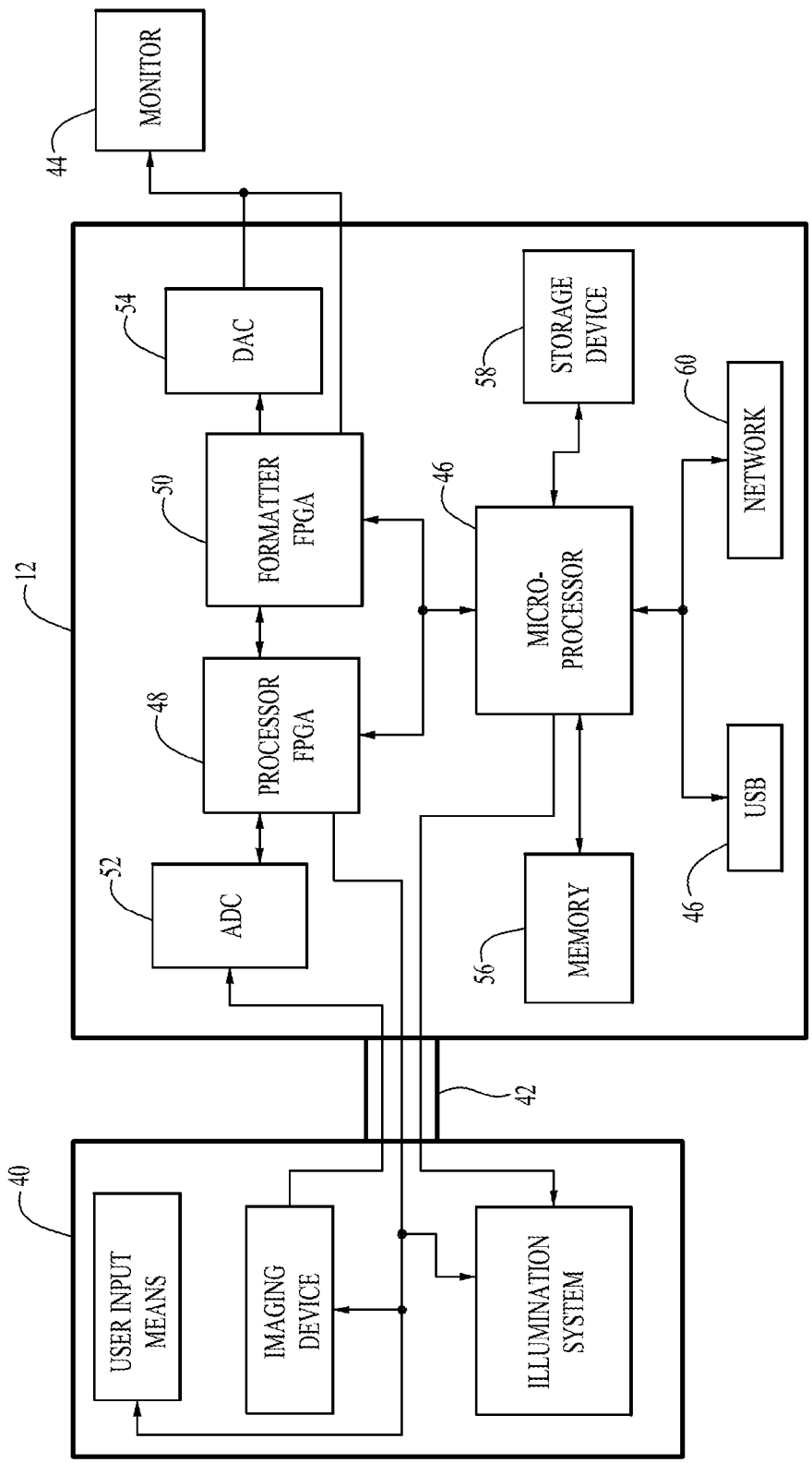
FIG. 2 is a schematic diagram illustrating a portion of a surgical imaging system in an operating room according to an additional embodiment of the present invention.

As shown in FIG. 2, the camera control unit 14 contains a microprocessor 46 for interfacing with user input devices, a signal processing circuit 48, a signal formatting circuit 50, analog to digital converters 52, digital to analog converters 54 and memory 56. The camera control unit 12 runs program applications providing for a variety of capabilities. For example, the camera control unit 12 may provide for a live feed of the image generated by the camera head 40 to be displayed through the monitor 44. Additionally, the camera control unit 14 may provide image capture functionality allowing for images generated by the camera head 12 to be saved to a storage device, such as an internal storage device 58 or a storage device external to the camera control unit. The captured images may be annotated or edited and displayed through the monitor 44.

The camera control unit 12 also has at least one network interface 60 that allows for the camera control unit 12 to access the network 18 and be accessed via the network 18. This allows the camera control unit, either directly or indirectly, to access information about other networked devices, such as operating room equipment. Operating equipment with information that may be accessed includes, for example and without limitation, shavers, fluid management systems, ablation devices, tourniquets and insufflators. Information about a pump accessible to the camera control unit may include, for example, modes, pressure and flow rate. Information about a shaver accessible to the camera control unit may include, for example, the number of revolutions per minute and the mode.

Additionally, the camera control unit 12 may be directly or indirectly coupled to additional cameras, such as an overhead camera in the operating room. Additionally, the camera control unit 12 may be connected to a microphone and speakers to allow, for example, a surgeon or other personnel to narrate what is happening and for music to be played.

According to an embodiment and with reference to FIG. 1, through the network interface 58, the camera control unit 12 may be directly or indirectly connected to the imaging system server 16 and may exchange information between the camera control unit 12 and local users 24, remote users 34, cloud storage 36 and the remote or control system 38. Local users 24 and remote users 34 may use computers and mobile computing devices, such as tablets, cellular phones and laptop computers. This may allow for streaming video of a procedure to be observed in real-time anywhere in the world.

For example, a program application for the camera control unit 12, data relevant to a particular patient or surgeon, and surgeon preferences may be stored on, or accessed by, the imaging system server 16 and used to quickly configure the camera control unit 12 for future sessions. Preferably, the camera control unit 12 can save images and video in different formats and to different places (e.g. internal memory, the system server 16, and to cloud storage 36 over the Internet).

The system server 16 preferably is a computer, such as an Apple Mac Mini® computer, containing a microprocessor, memory, video processor and network interface. The system server 16 may be a dedicated file server with redundant storage mechanisms, such as a Dell Poweredge® server. Preferably, the system server 16 runs an operating system such as Microsoft Windows® or Microsoft Server®. Preferably, the system server 16 operates as a web host, thereby allowing information to be accessed by local users and remote users with readily available software, such as via a web browser. The system server 16 may be a virtual machine and may be located for example on an existing hospital server.

The system server 16 has access to databases that contain global data for the camera control units in the system. Preferably, the databases contain information about for example surgeon preferences, patient information, case lists and equipment preferences. Preferably, the system server 16 has access to institution servers or datastores (for example, an electronic medical record (EMR) server, picture archiving and communication systems (PACS) server or datastore), obtains information (for example, patient information) from the servers or datastores, and saves information (such as data and images) to the servers or datastores. In an embodiment, the system server translates data and images from different formats.

Although the term "surgeon preferences" is used below for illustrative purposes, the preferences stored by the system, may also include preferences of doctors, staff and hospitals for operation of various aspects of the system. The surgeon preferences may include, for example, default camera settings, camera head input button functions, image saving locations, and image file types. Preferably, the surgeon preferences may be specific to procedure types. For example, default camera settings for a given surgeon may change depending on the type of procedure being performed. Once the camera control unit determines the surgeon and the procedure being performed, then the camera control unit may load proper default camera settings for the surgeon thereby increasing efficiency and preventing errors. Any changes made to the surgeon preferences (either through the camera control unit, or by a local or remote user) are then saved to the system server 16.

The databases may contain additional information about surgeon preferences. For example, the databases may contain preferences for equipment settings for different types of surgeries, and for music played during a particular type of surgery. The databases may contain preferences about whether and in what situations text messaging during surgery is allowed, about whether and what situations remote viewers may watch procedures. For example, the surgeon may specify in their preferences which users may text during procedure and which users may remotely view a procedure and may further customize this based on the procedure type.

The preferences may also include, for example, what information is displayed on the surgical monitor. Some surgeons may not want any data overlaying the surgical image. Additionally, a surgeon may only want information about a particular surgical appliance if certain preconditions are met (e.g. if a pump system is operating over a certain pressure), or if there is an operating error (e.g. the printer is out of paper). A surgeon may also customize the information that is displayed depending on the type of procedure.

The databases may also contain preferences about image and data management for post-operative reporting. For example, the databases may contain default report formats for post-operative reports for institution records, referring physicians, patients, surgeons and insurance. The databases may configure the reports with certain pre-filled information depending on the report type, surgeon, patient type and procedure type.

For example, a report for a particular type of surgery may be electronic, with a link to the report being sent to a patient. When the patient opens the link, their computer may be securely directed to a web address generated by the system server 16 or another server that then provides the patient with video, still images, links to documents and postoperative care instructions. Additionally, a report for an insurance company may be prefilled with relevant current procedural technology (CPT) codes depending on the type of procedure performed and the physician to help automate the process for reimbursement. Multiple reports may be created at once and sent to multiple locations.

In an additional embodiment of the present invention, the camera control unit 12 is able to display more than one video stream at a time on the surgical monitor 44. For example, because the camera control unit 12 is connectable to multiple video streams over the network 18, the camera control unit may cause video from multiple camera heads within the operating room to be displayed (for example, in a surgery where multiple endoscopic cameras are being used to visualize a surgical site). Additionally, the camera control unit 12 may cause video from a different operating room to be displayed, so that for example, the surgeon can give advice to a surgeon in a different operating room.

Optionally, the system 10 utilizes the cloud storage 36 to store information about cases for a surgeon or other user. Preferably, the information saved on the cloud storage 36 includes all relevant data associated with a case. The particular information saved to the cloud storage 36 may be specified in user preferences saved in a database accessible to the camera control unit 12. Saved information may include, for example, demographic data of patient, what equipment was used and surgical artifacts, including images and video. Access to the cloud storage will preferably be controlled by an authentication database linked to the system server 16. A surgeon or other user may log into the cloud storage from any device having a web browser, access the information and prepare reports.

Preferably, the system server 16 and the cloud server 36 provide an interface for the surgeon to edit surgical artifacts (for example, to crop, enhance and annotate surgery photos, crop, edit and annotate surgery videos), save the edited artifacts and add the edited artifacts to reports using a web browser. Additionally, the system server 16 or the cloud server interface may allow a surgeon to share information with colleagues such as via email. The surgeon may record additional artifacts, such as an audio or video file explaining things to a patient (e.g. "surgery went well, wash the area with warm water and mild soap twice a day") or a colleague and save those artifacts for later inclusion in a report.

Specific applications of the system of the present invention according to various embodiments will now be described. The descriptions below are for illustrative purposes and are not intended to limit the invention to the specific embodiments described.

Remote Viewing and Communication

In an embodiment, a local user 24, such as a nurse at a station outside the operating rooms of a hospital, or a remote user 34, such as a doctor located at a different hospital, logs into the system server 16 using a web browser, such as Microsoft Internet Explorer®, Mozilla Firefox®, Google Chrome® or Apple Safari®, or other client software, such as Microsoft Windows® remote desktop. In order to facilitate security, preserve physician and patient information and to comply with the Health Insurance Portability and Accountability Act of 1996 (HIPAA) privacy and security rules, a database of authorized users and passwords is maintained on, or accessed by, the system server 16 and used by the system server 16 to authenticate users.

Figure 3:
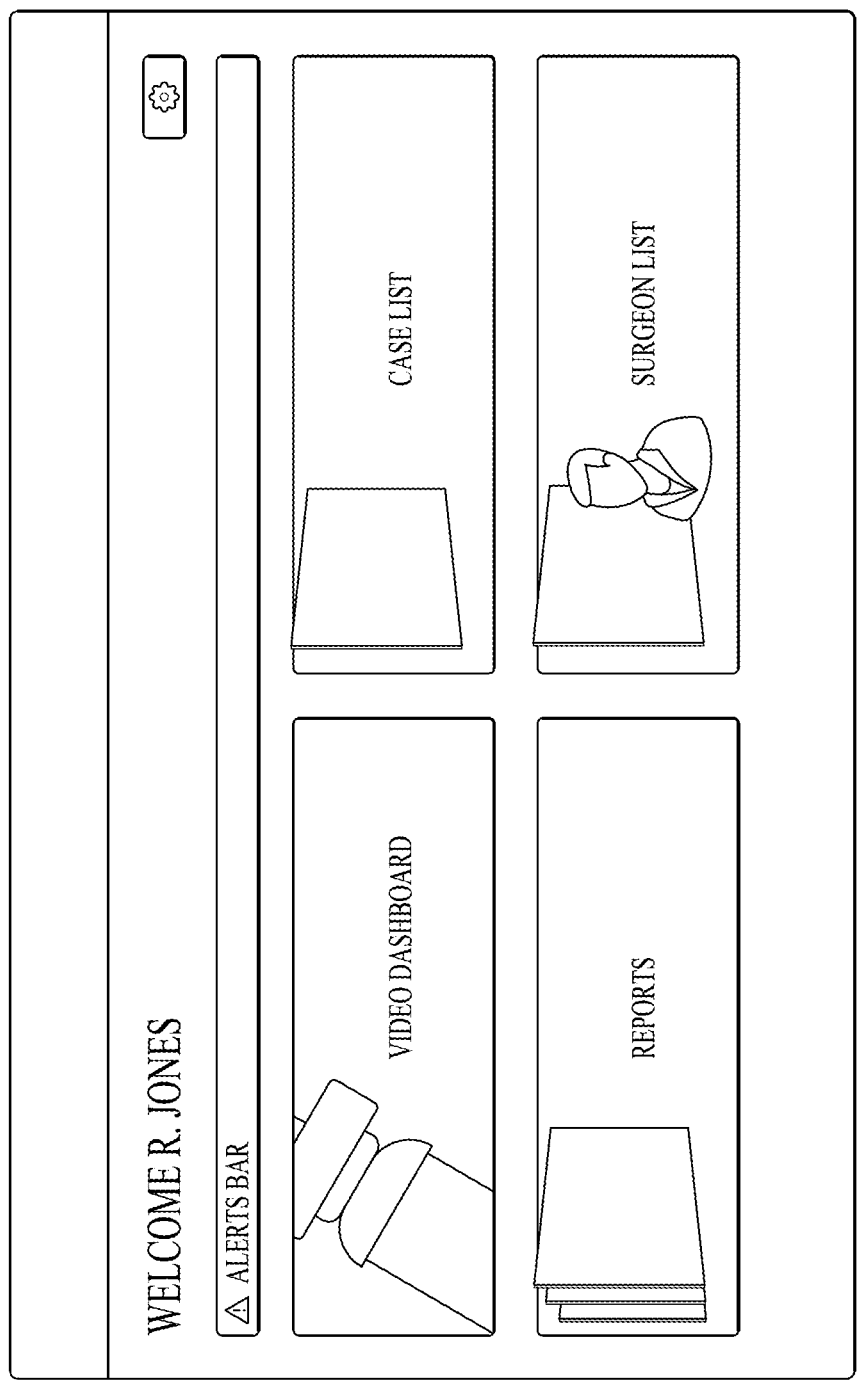
FIG. 3 is a screenshot showing a welcome screen seen by a local or remote user after logging onto the system server according to an embodiment of the present invention.

Once a user has entered identification and appropriate security credentials, the user is allowed access to information on the server 16 and may be presented with a welcome screen such as that depicted in FIG. 3. The welcome screen may present the user with a choice of different options, such as the option to check the status of various institution operating rooms and view images from surgeries in progress (video dashboard), obtain a list of cases for review (case list), view and make reports (reports) and view a list of surgeons (surgeon list). The option screen may be customized for different types of users. For example, certain users may not be given access to the case list or the surgeon list. The permissions may be stored with security credentials in the system server 16.

Figure 4:
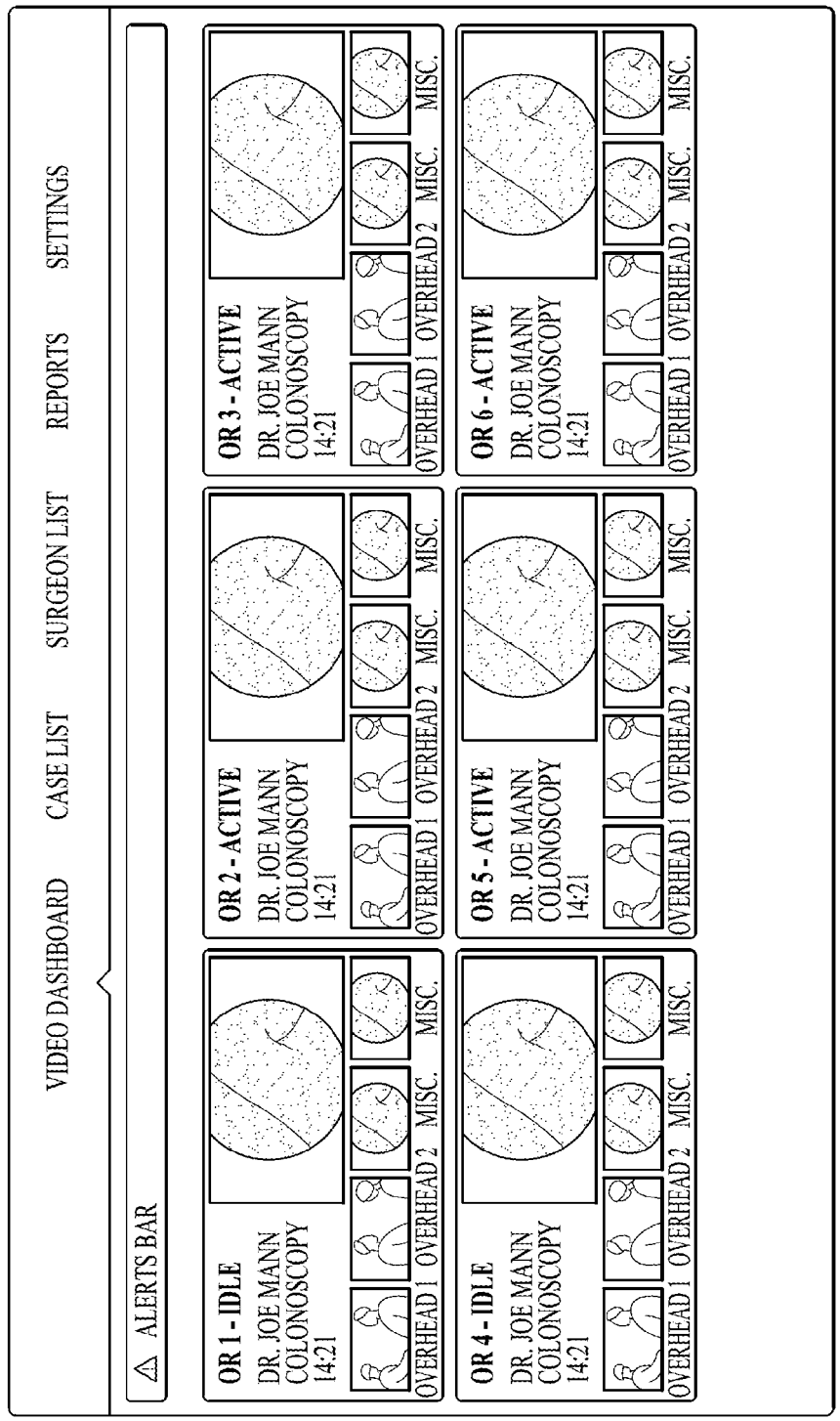
FIG. 4 is a screenshot showing a view of the activity in each operating room of an institution according to an embodiment of the present invention.

If the user selects video dashboard, then the user may be presented with a screen such as that depicted in FIG. 4. A video dashboard screen according to an embodiment of the present invention presents a user interface to conveniently show data and video for a remote or local user. The data include relevant information such as the state of the camera control unit ("Idle/Active"), the surgeon name, procedure type, surgery time, and relevant alerts (e.g. "printer is out of paper") in a given operating room. The video sources may include for example endoscopy video from the camera control unit and an over-head camera if available.

To enable viewing of multiple video streams on a browser based device with limited computing power, the system server 16 in combination with the camera control units may adaptively provide a series of low frequency (such as 2 Hz) still images when the browser is displaying more than 2 video sources at a time. This eliminates the need to instantiate multiple software based decoders on the remote device (which may be a mobile computing device with limited hardware capability) which would tax the processing capability of the remote device and may lead to poor performance.

In an embodiment of the present invention, the camera control unit in a given operating room provides a series of still images for access by the system server 16. In an additional embodiment of the present invention, each camera control unit forwards video from any camera heads or other cameras coupled to the camera control unit to the system server 16 for processing, storage and distribution. Video data may be sent from the camera control unit to the system server in an HTTP-based media stream communication protocol such as HTTP Live Streaming (HLS).

In an embodiment, each camera control unit is configured as a web host and places the series of still images at a specific web address (URL) accessible by the system server 16. Additionally, each camera control unit may provide one or more streaming video feeds at a specific web address accessible by the system server 16. Software on the system server 16 causes the system server to adaptively access the URL for streaming video(s) when 1 or 2 streams are being displayed. The system server 16 may adaptively access the URL for still images when more than 2 "streams" are being displayed simultaneously for a user.

Figure 5:
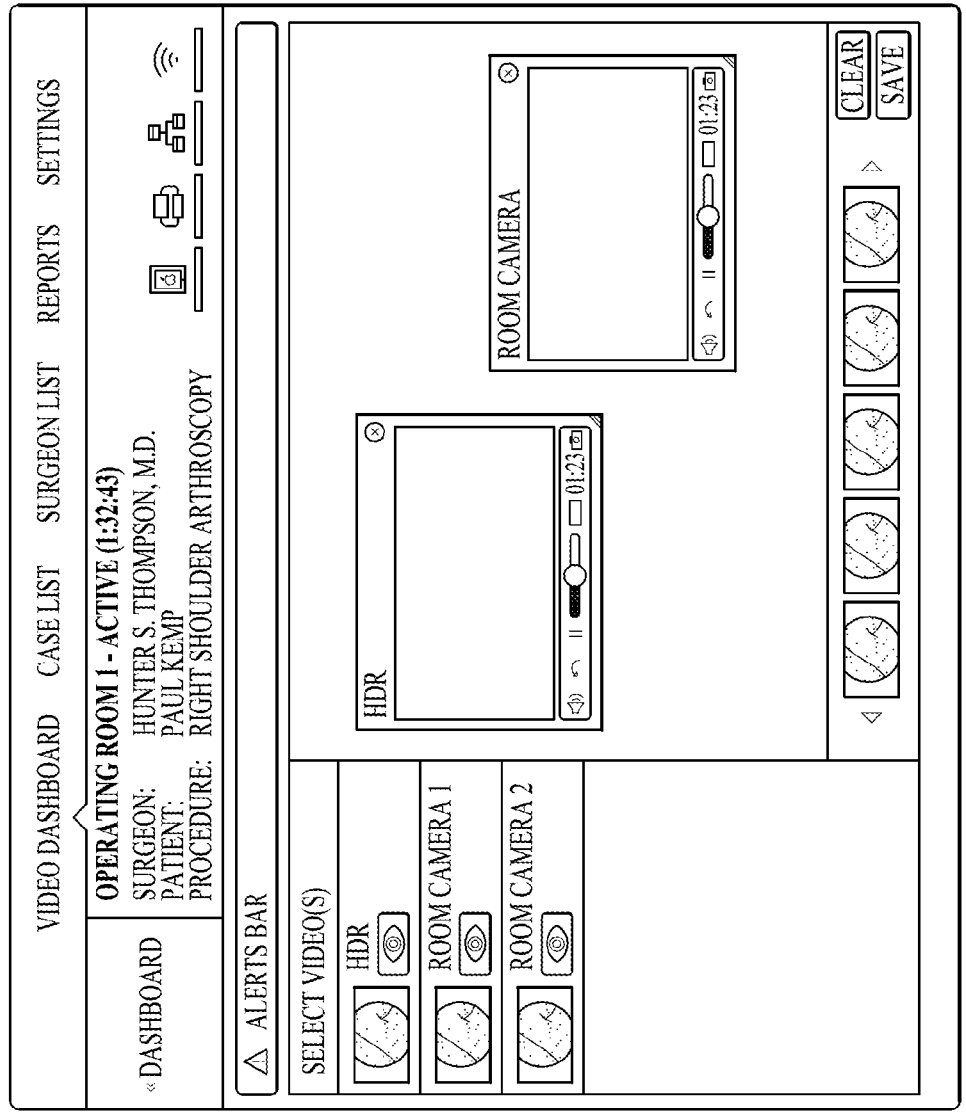
FIG. 5 is a screenshot showing a view of the activity in a specific operating room according to an embodiment of the present invention.

If the user selects a specific operating room for review, the user may be presented with a screen such as that shown in FIG. 5. In addition to any available video for a single operating room, a user may be presented with still images, alerts specific to the viewed operating room, and the state of connected devices (e.g. iPad, printer, or network).

In an embodiment, the single operating room screen may enable a user to communicate with the surgeon inter-operatively, such as via a text chat box. In the chat box, the remote viewer can type or use voice to text capability available in some devices to create a text message to the surgeon. The system server 16 would then, based on the surgeon's preference either deny or forward the text message to the camera control unit for display on the surgical monitor 44 as shown in FIG. 6.

In an embodiment, prior to displaying the text message on the surgical monitor 44, the camera control unit 12 prompts the surgeon to approve text messaging. If the surgeon declines text messaging, then a message may be sent by the system server 16 to the user notifying the user that the surgeon has declined text messaging. If the surgeon approves text messaging, then the text message may be displayed on the monitor 44 along with sender identification information. In an embodiment, the surgeon may verbally respond to the text message with a microphone coupled to the camera control unit 12 and an audio stream of the surgeon's response is sent along with any streaming video. Additionally, the surgeon may verbally respond with the response then translated to text by the camera control unit 12 and the resulting text sent to the user.

Figure 6:
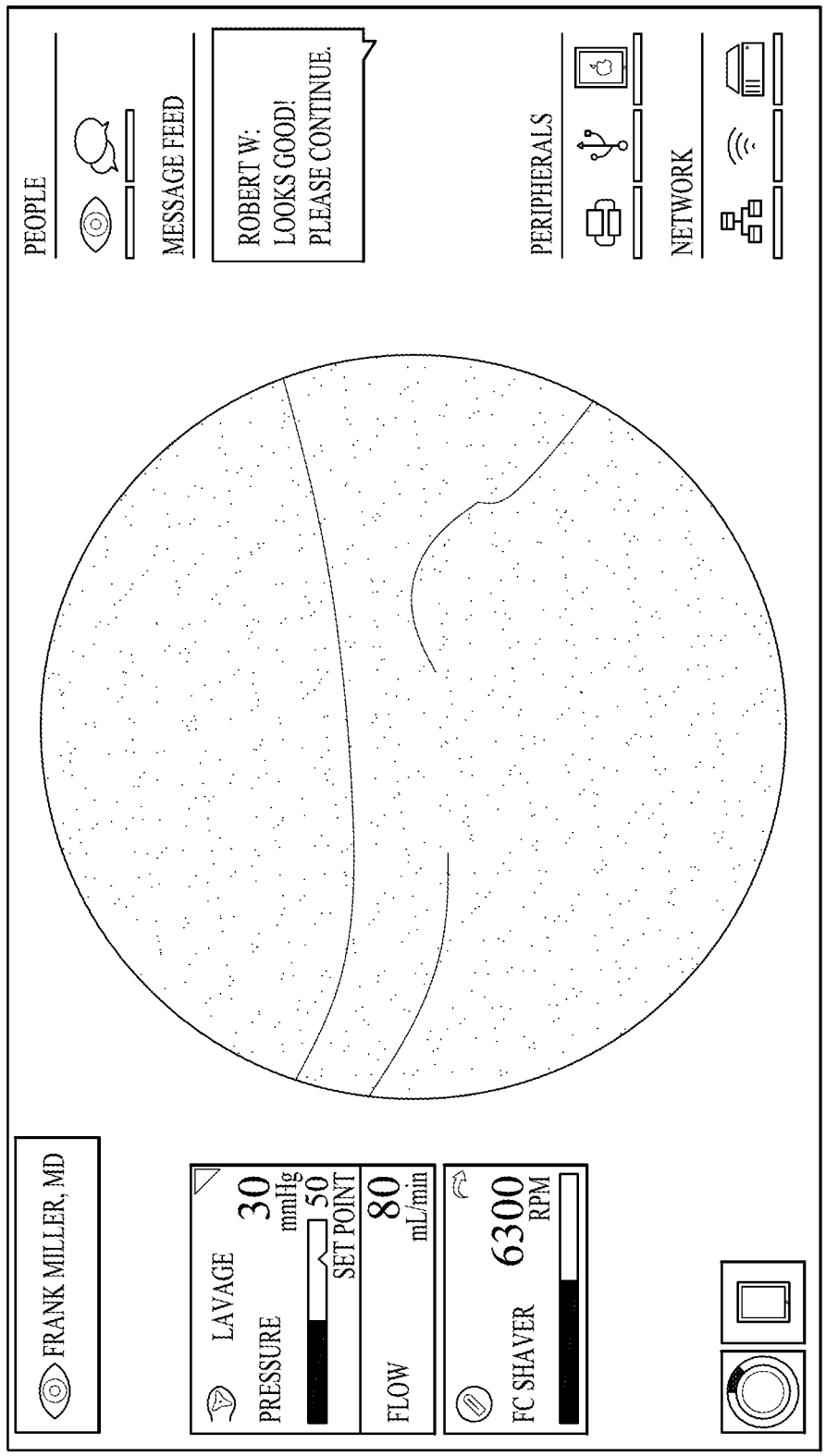
FIG. 6 is a screenshot showing a view of a surgical monitor and the status of surgical equipment in the operating room and text messaging according to an embodiment of the present invention.

FIG. 6 shows the surgical monitor displaying information in addition to the text messaging. Because the camera control unit 12 may communicate with networked appliances such as, for example, shavers and irrigation systems (pumps) as well as peripherals, such as printers, wired networks, wireless networks and input devices, the camera control unit 12 may overlay surgical video on the monitor 44 with information about the networked appliances and peripherals. The camera control unit 12 may also overlay surgical video with additional information about the presence of locals users, remote users, status updates, calendar and schedule information, doctor, patient, or procedure.

Data Management

According to an embodiment of the present invention, the system server 16 provides a means to store and direct data and associated artifacts (e.g. images, videos) for post-operative management. As shown in FIG. 3, the welcome screen provides an authorized user (such as surgeons or specific hospital staff) an option to manage surgeon preferences such as those discussed above and for post operative management of data and artifacts. As explained above, the surgeon preferences are stored in a database (such as an SQL database) accessible to the system server 16. The system server 16 synchronizes the database with local databases stored on the camera control units. This enables multi-point data management from the camera control units and from the user interface available to users from the system sever 16 with one central database repository. If a camera control unit 12 is removed from the network 18, or if the network fails, all preference information remains in each camera control unit so that it can operate independently. Similarly, image and video data stored on each camera control unit remains intact if the camera control unit is disconnected from the network. Synchronization resumes when the network connection is reestablished.

Figure 7:
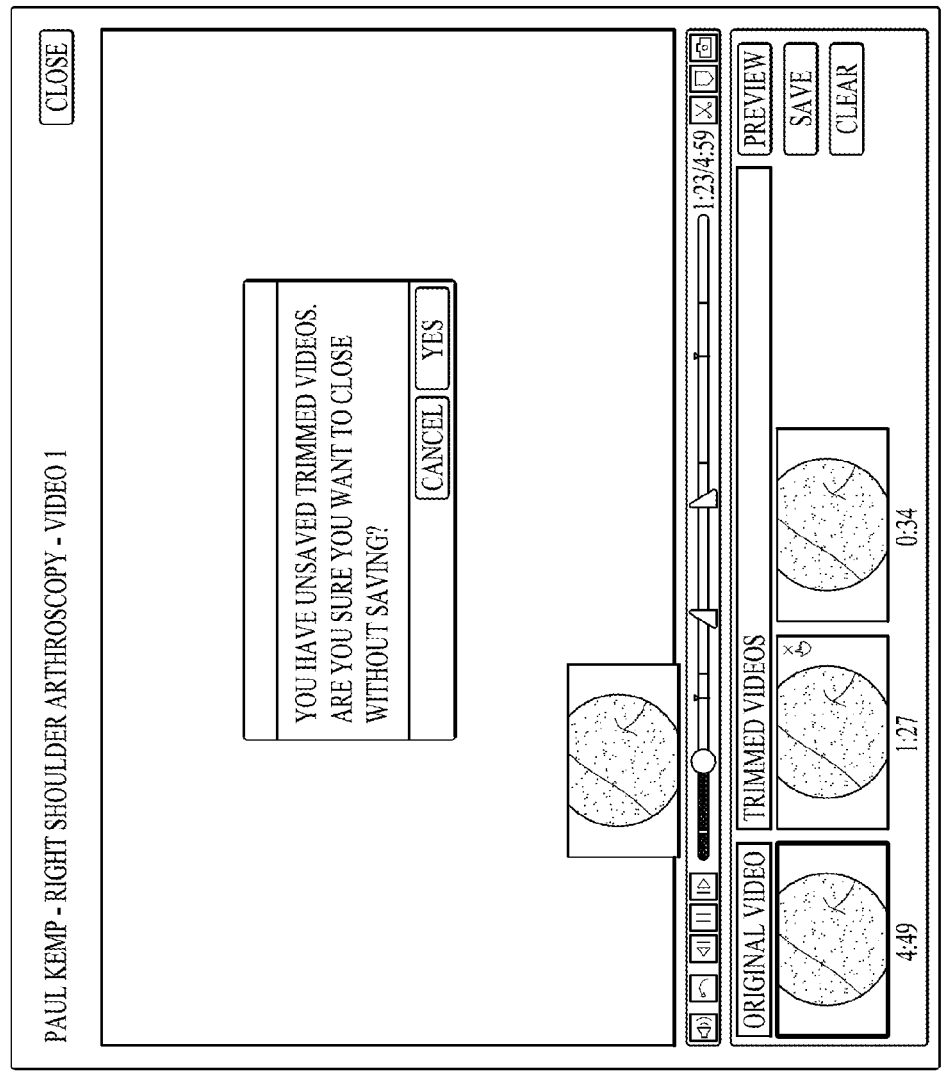
FIG. 7 is a screenshot showing a video editing screen available to a local or remote user according to an embodiment of the present invention.
Figure 8:
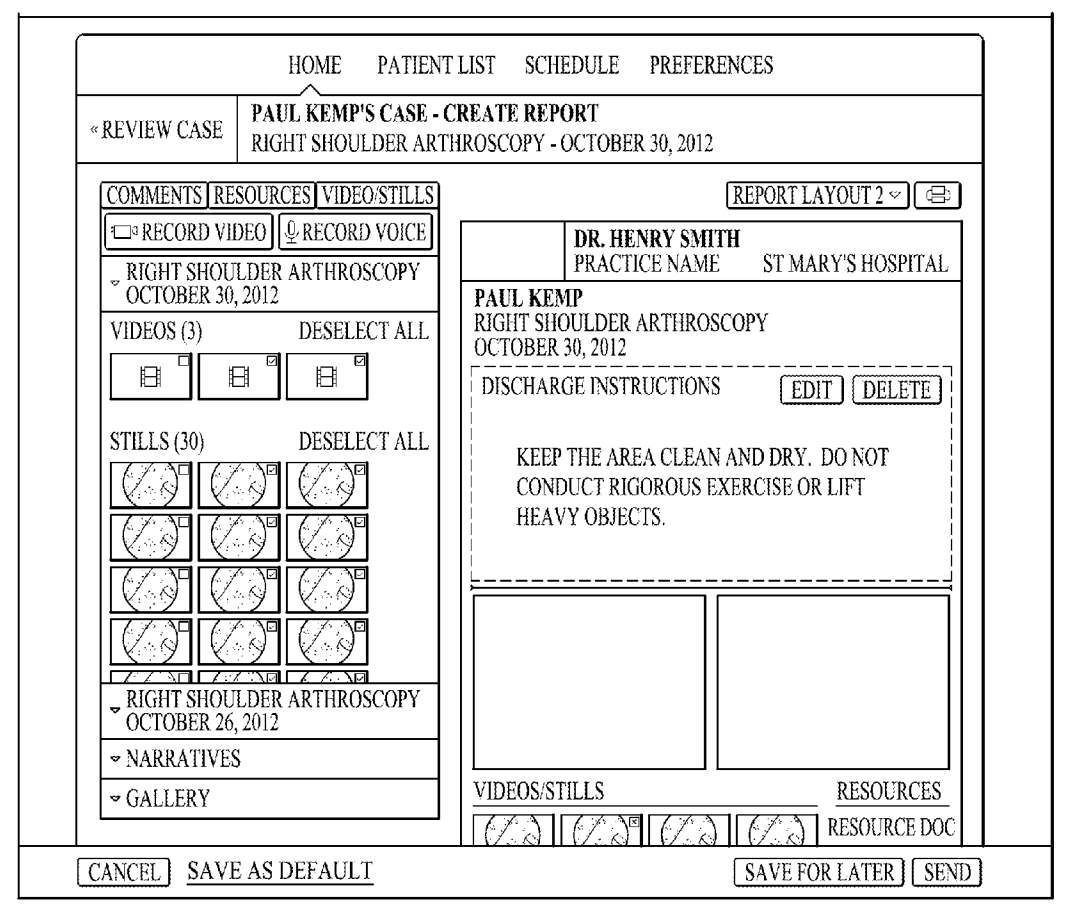

The system server 16 synchronizes to the cloud storage 36 with active synchronization upon a database update from a camera control unit or the system server 16. Preferably, the system server 16 or the cloud server 36 provides an interface for the surgeon as a local user 24 or remote user 34 via a web browser to edit surgical artifacts (for example, to crop, enhance and annotate surgery photos; and to crop, edit and annotate surgery videos) and save the edited artifacts as shown in FIG. 7. The system server 16 or the cloud storage 36 provides an interface for the surgeon as a local user 24 or remote user 34 via a web browser to create reports with surgery data, surgical artifacts, links to documents and postoperative care instructions as shown in FIG. 8.

Reporting

With the system server 16 in communication with the camera control units and the resident database, there is stored data that can be mined and analyzed for efficiency of the operating room and equipment performance as shown in FIGS. 9 and 10. The system may automatically log the start time of a procedure based on, for example, when a surgeon or staff opens a specific case, when a camera head is connected or when a white balance is first done. Likewise, the system may automatically log the end time of a procedure based on, for example, when the surgeon/staff closes a specific case or when a camera head is disconnected. The system may also routinely log settings and error messages of networked equipment.

This information is useful to cut costs and to standardize medical practices, eliminate variability, and improve surgical outcomes. The database can be queried based on desired criteria. For example, a report may be created for surgery duration (surgery start time—surgery end time) for all procedures of a given type (for example, ACL reconstructions) performed over a given period (for example, the last 6 months) by a given surgeon. This may show how one surgeon compares to another for the same type of procedure. Additionally, operating room turn-around time may be analyzed.

Comparisons may be made of different operating rooms, surgeons, staff and equipment in many different respects. For example, the system can compare the number of still images, printouts, equipment settings and other performance attributes of different surgeons. Anything wrong with specific devices may be logged and analyzed.

Changes to the configuration of specific devices may be logged automatically. This may be helpful in situations where the settings of specific devices are required to be manually logged (such as with changes made to ablation device settings). These changes may be automatically uploaded to the patient's records stored on an institution server or datastore 20 such as an electronic medical record (EMR) system.

As shown in FIG. 11, the present invention according to an additional embodiment, is directed to a system for sharing data and images among multiple (a cluster of) camera control units 100, additional sources and sinks, and a system server 102 employing a separate network with a single switch 104 that supports both 10/100 Ethernet and 10 gigabit (10 Gb) fiber connectivity rather than requiring separate switches and networks. Preferably, the 10/100 Ethernet connections and the 10 gigabit fiber connections are configured on separate virtual local area networks (VLANs) on the switch to keep the traffic separate and prevent network collisions.

In this embodiment, the system server 102 functions as described above, but is part of a network that may be isolated by a firewall 106, or similar technology, from a facility network and from a wide area network (WAN) such as the Internet. The single firewalled connection to the facility network or the Internet segments traffic and adds a layer of security.

This construction allows the system to be built, configured and tested remotely from a facility where the system is to be installed. Once built, configured and tested, the system can be quickly installed, thereby reducing installation time. The use of 10 gigabit fiber allows for very high quality video and images, and multiple streams of high quality videos and images to be passed between camera control units 100, additional sources 110 such as C-Arms and operating room cameras, and sinks 112 such as displays, while still preserving the functionality described above for remote viewing and communication, data management and reporting.

As shown in FIG. 11, preferably each camera control unit 100 is coupled to a separate wireless router 108, thereby providing local wireless access for streaming and management without having to utilize facility wireless infrastructure, thereby diminishing the load on the facility's network.

There is disclosed in the above description and the drawings, a surgical imaging system and method for processing surgical images that fully and effectively overcomes the disadvantages associated with the prior art. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. §112.

What is claimed is:

1. An imaging system comprising:
    at least two surgical systems, each surgical system further comprising:
        a camera control unit, each camera control unit further comprising a network port;
        a camera head coupled to the camera control unit; and
        a monitor coupled to the camera control unit;
    a network coupled to the network port of each camera control unit;
    a server coupled to the network, the server comprising a storage device comprising a user database and a case database;
    wherein the server is configured as a web server to provide data, video and images from the camera control units to users connected to the network,
    wherein the user database further comprises user preferences for who can view at least one of live surgical data, video and surgical images; and wherein the system server provides at least one of live surgical data, video and surgical images to users connected to the network in accordance with the user preferences and wherein the server is further configured to allow text messaging, audio conferencing or videoconferencing between a user connected to the network and at least one camera control unit; the user database further comprises user preferences for who can engage in text messaging, audio conferencing or videoconferencing; and wherein the server provides text messaging, audio conferencing or videoconferencing between a user connected to the network and the at least one camera control unit in accordance with the user preferences.

2. The imaging system of claim 1 wherein the user database further comprises user preferences for a camera control unit; and wherein each camera control unit is configurable by the server to have the user preferences.

3. The imaging system of claim 1 wherein:
each surgical system further comprises at least one surgical device in communication with the camera control unit;
the user database further comprises user preferences for displaying information from the at least one surgical device on the monitor; and
the server uses the user preferences to configure each camera control unit to display information from the at least one surgical device on the monitor.

4. The imaging system of claim 3 wherein the at least one surgical device is selected from the group consisting of: a shaver, a pump, an ablation device, a tourniquet and an insufflator.

5. The imaging system of claim 1 wherein:
each surgical system further comprises at least one surgical device in communication with the camera control unit;
the user database comprises user preferences for the at least one surgical device; and
the server uses the user preferences for the at least one surgical device to configure the at least one surgical device.

6. The imaging system of claim 5 wherein the server stores information from the at least one surgical device and surgical data, video and surgical images in the case database.

7. The imaging system of claim 1 further comprising at least one storage device coupled to the network; the user database further comprises user preferences about data, video and images stored on the storage device; and wherein the server stores data, video and images on the storage device in accordance with the user preferences about data, video and images stored on the storage device.

8. The imaging system of claim 7 wherein the user database further comprises user preferences for generating reports; and wherein the server is further configured to generate reports from data, video and images in the case database for at least one of the group consisting of institutions, referring physicians, patients, surgeons and insurance companies in accordance with the user preferences for generating reports.

9. The imaging system of claim 7 wherein the user database further comprises user preferences for generating reports; wherein the storage device is configured as a web server to provide data and images to users and to generate reports for at least one of the group consisting of institutions, referring physicians, patients, surgeons and insurance companies in accordance with the user preferences for generating reports.

10. The imaging system of claim 9 wherein the storage device is further configured to allow users to edit or annotate at least one of surgical data, video and images and save the edited or annotated surgical data, video and images.

11. The imaging system of claim 1 wherein the server is configured to provide data, video and images from more than one camera control unit simultaneously to users connected to the network.

12. The imaging system of claim 11 wherein each camera control unit is configured as a web server to provide reduced resolution video, reduced frame-rate video or still images from the camera head; and wherein the server is configured to obtain the reduced resolution video, reduced frame-rate video or still images from the camera control unit.

13. An imaging system comprising:
at least two surgical systems, each surgical system comprising:
a camera control unit, each camera control unit comprising a network port;
a camera head coupled to the camera control unit;
a monitor coupled to the camera control unit; and
at least one surgical device in communication with the camera control unit;
a network coupled to the network port of each camera control unit;
a server coupled to the network, the server comprising a storage device having a user database and a case database; and
wherein the server is configured as a web server to provide data, video and images from the camera control units to users connected to the network; and
wherein the server is further configured to allow text messaging, audio conferencing or videoconferencing between a user connected to the network and at least one camera control unit; the user database further comprises user preferences for who can engage in text message, audio conferencing or videoconferencing; and wherein the system server provides text messaging, audio conferencing or videoconferencing between a user connected to the network and the at least one camera control unit in accordance with the user preferences.

14. The imaging system of claim 13 wherein:
the user database further comprises user preferences for the at least one surgical device;
the server uses the preferences for the at least one surgical device to configure the at least one surgical device; and
the server uses the preferences for the at least one surgical device to configure each camera control unit to display information from the at least one surgical device on the monitor.

15. The imaging system of claim 13 wherein the server stores information from the at least one surgical device, video and images in the case database.

16. The imaging system of claim 13 wherein the at least one surgical device is selected from the group consisting of: a shaver, a pump, an ablation device, a tourniquet and an insufflator.

17. An imaging system comprising:
at least two surgical systems, each surgical system comprising:
a camera control unit, each camera control unit comprising two network ports;
a camera head coupled to the camera control unit;
a monitor coupled to the camera control unit; and
at least one surgical device in communication with the camera control unit;
a first network coupled to a first network port of each camera control unit;
a second network coupled to a second network port of each camera control unit, the second network comprising a different bandwidth than the first network;
a switch coupled to the first network and the second network;

a server coupled to the switch, the server comprising a storage device having a user database and a case database;

wherein the server is configured as a web server to provide data, video and images from more than one camera control unit simultaneously to users connected to the network; and wherein the server is further configured to allow text messaging, audio conferencing or videoconferencing between a user connected to the network and at least one camera control unit; the user database further comprises user preferences for who can engage in text message, audio conferencing or videoconferencing; and wherein the server provides text messaging, audio conferencing or videoconferencing between a user connected to the network and the at least one camera control unit in accordance with the user preferences.

18. An imaging system comprising:

at least two surgical systems, each surgical system further comprising:
  a camera control unit, each camera control unit further comprising a network port;
  a camera head coupled to the camera control unit; and
  a monitor coupled to the camera control unit;
a network coupled to the network port of each camera control unit;
a server coupled to the network, the server comprising a storage device comprising a user database and a case database; and
wherein the server is configured as a web server to provide data, video and images from the camera control units to users connected to the network; and
wherein the server is further configured to allow text messaging, audio conferencing or videoconferencing between a user connected to the network and at least one camera control unit; the user database further comprises user preferences for who can engage in text messaging, audio conferencing or videoconferencing; and wherein the server provides text messaging, audio conferencing or videoconferencing between a user connected to the network and the at least one camera control unit in accordance with the user preferences.

19. The imaging system of claim 18 wherein the user database further comprises user preferences for a camera control unit; and wherein each camera control unit is configurable by the server to have the user preferences.

20. The imaging system of claim 18 wherein:

each surgical system further comprises at least one surgical device in communication with the camera control unit;
the user database further comprises user preferences for displaying information from the at least one surgical device on the monitor; and
the server uses the user preferences to configure each camera control unit to display information from the at least one surgical device on the monitor.

21. The imaging system of claim 20 wherein the at least one surgical device is selected from the group consisting of: a shaver, a pump, an ablation device, a tourniquet and an insufflator.

22. The imaging system of claim 18 wherein:

each surgical system further comprises at least one surgical device in communication with the camera control unit;
the user database comprises user preferences for the at least one surgical device; and
the server uses the user preferences for the at least one surgical device to configure the at least one surgical device.

23. The imaging system of claim 22 wherein the server stores information from the at least one surgical device and surgical data, video and surgical images in the case database.

24. The imaging system of claim 18 further comprising at least one storage device coupled to the network; the user database further comprises user preferences about data, video and images stored on the storage device; and wherein the server stores data, video and images on the storage device in accordance with the user preferences about data, video and images stored on the storage device.

25. The imaging system of claim 24 wherein the user database further comprises user preferences for generating reports; and wherein the server is further configured to generate reports from data, video and images in the case database for at least one of the group consisting of institutions, referring physicians, patients, surgeons and insurance companies in accordance with the user preferences for generating reports.

26. The imaging system of claim 24 wherein the user database further comprises user preferences for generating reports; wherein the storage device is configured as a web server to provide data and images to users and to generate reports for at least one of the group consisting of institutions, referring physicians, patients, surgeons and insurance companies in accordance with the user preferences for generating reports.

27. The imaging system of claim 26 wherein the storage device is further configured to allow users to edit or annotate at least one of surgical data, video and images and save the edited or annotated surgical data, video and images.

28. The imaging system of claim 18 wherein the server is configured to provide data, video and images from more than one camera control unit simultaneously to users connected to the network.

29. The imaging system of claim 18 wherein each camera control unit is configured as a web server to provide reduced resolution video, reduced frame-rate video or still images from the camera head; and wherein the server is configured to obtain the reduced resolution video, reduced frame-rate video or still images from the camera control unit.

* * * * *